United States Patent [19]
Miles et al.

[11] Patent Number: 5,625,147
[45] Date of Patent: Apr. 29, 1997

[54] APPARATUS AND METHOD FOR MONITORING THE EATING QUALITY OF MEAT

[75] Inventors: Christopher A. Miles, Bristol; Christopher C. Warkup, Milton Keynes, both of United Kingdom

[73] Assignee: Meat and Livestock Commission, Milton Keynes, United Kingdom

[21] Appl. No.: 500,973

[22] PCT Filed: Feb. 4, 1994

[86] PCT No.: PCT/GB94/00203

§ 371 Date: Aug. 7, 1995

§ 102(e) Date: Aug. 7, 1995

[87] PCT Pub. No.: WO94/18554

PCT Pub. Date: Aug. 18, 1994

[30] Foreign Application Priority Data

Feb. 10, 1993 [GB] United Kingdom ............... 9302601

[51] Int. Cl.⁶ ....................... G01N 29/08; A61B 10/00
[52] U.S. Cl. ................. 73/597; 73/599; 73/646; 128/660.07
[58] Field of Search ............... 73/597, 599, 645, 73/646, 647; 128/660.07

[56] References Cited

U.S. PATENT DOCUMENTS

| 3,345,863 | 10/1967 | Henry et al. ............... 73/597 |
| 3,964,297 | 6/1976 | Jorgensen et al. ............ 73/67.8 R |
| 4,009,390 | 2/1977 | Sattlerlee et al. ........... 250/273 |
| 4,099,420 | 7/1978 | Stouffer et al. ............. 73/629 |
| 4,785,817 | 11/1988 | Stouffer ..................... 73/602 |
| 5,079,951 | 1/1992 | Raymond et al. ............... 73/602 |
| 5,140,988 | 8/1992 | Stouffer et al. ............. 128/660.07 |

FOREIGN PATENT DOCUMENTS

| 0337661 | 10/1989 | European Pat. Off. . |
| 0523865 | 1/1993 | European Pat. Off. . |
| 3619292 | 10/1987 | Germany . |
| 246311 | 11/1995 | New Zealand . |
| 665261 | 5/1979 | Russian Federation . |
| 2213263 | 9/1989 | United Kingdom . |
| WO93/12419 | 6/1993 | WIPO . |

*Primary Examiner*—Robert Raevis
*Assistant Examiner*—Rose M. Finley
*Attorney, Agent, or Firm*—Sterne, Kessler, Goldstein & Fox, P.L.L.C.

[57] ABSTRACT

A method and apparatus for obtaining information relating to the eating quality of meat. The meat under test may include a hot or cold meat carcass, raw or cooked meat or live animal. The method includes the steps of injecting an acoustic signal into the meat, monitoring the effect of the meat on at least one characteristic of the acoustic signal propagated into the meat, and applying the monitored effects to a predetermined algorithm relating eating quality to monitored acoustic effects to indicate the eating quality of the meat under test. The acoustic probe assembly of the apparatus includes a pair of arms adapted for insertion into a meat carcass. The arms carry respective means for coupling acoustic signals into and receiving signals from the carcass. Further, the arms include means for coupling the acoustic signals to the surface of a carcass and monitoring scattering of the acoustic signals to predict the eating quality of meat.

19 Claims, 2 Drawing Sheets

APPARATUS AND METHOD FOR MONITORING THE EATING QUALITY OF MEAT

The invention relates to methods and apparatus for monitoring the eating quality of meat.

Many different techniques already exist for investigating meat carcasses to obtain information relating to their physical characteristics. These include techniques for measuring quality traits such as pH, colour, drip, and intramuscular fat as well as taste panel assessments.

Ultrasonic techniques are now widely used throughout the world to assess the body and carcass composition of farm livestock. Ultrasonic inspection of homogenised meat has contributed substantially to understanding the nature of the phenomena taking place when ultrasound is transmitted through tissue and has also generated the ideas for improved equipment for determining carcass composition. In the future that equipment is likely to be more widely used and could replace existing pulse-equipment as the equipment of choice for examining farm livestock.

Techniques for inspecting meat can be divided into different areas. These include techniques for looking at carcass composition or carcass quality (the fat:lean ratio); techniques for looking at muscle quality such as colour, fat content, wetness, and muscle structure (smooth/grainy); and techniques using taste panel assessments for determining eating quality which may be characterised as tenderness, juiciness/succulence, and flavour.

Many techniques exist for determining carcass composition and muscle quality. Thus, GB-A-2213263 discloses a method for determining body composition of an animal and in this case the technique is determining carcass composition.

EP-A-0523865 discloses another technique for monitoring carcass composition.

EP-A-0499765 describes an ultrasonic technique for obtaining information about a carcass and uses a correlation technique to compare the effects of the carcass on the ultrasound with a correlation table to indicate physical characteristics of the carcass including the thickness of meat layers, the thickness of fat layers, fleshiness, "fat marbling", or the meat/fat pattern, the structure of the meat fibres, the structure of connective tissue, the water content, the amount of PSE- and DFD-meat, and the ability of the meat body to bind the meat juice therein.

None of these techniques have been successful in predicting eating (or organoleptic) quality from the predetermined physical characteristics. Attempts have been made to predict eating quality as for example is described in De Vol, D. L., McKeith, F. K., Bechtel, P. J., Novakovski, J., Shanks, R. D. and Carr, T. R. (1988). "Variation in composition and palatability traits and relationships between muscle characteristics and palatability in a random sample of pork carcases". J. Anim. Sci. 66: 385–395. De Vol et al found that using a number of physical parameters of pork including colour, marbling score and intramuscular fat measured chemically, only a small proportion of the variation in tenderness and juiciness could be explained, 21% and 26% respectively. These values correspond to multiple correlations of approximately r=0.46 and r=0.51 respectively.

Other work has confirmed the difficulties which have been found until now. Wood, J. D. and Warris, P. D. (1992). "The influence of manipulation of carcase composition on meat quality", in "The control of fat and lean deposition", edited by Boorman, K. N., Buttery, P. J. and Lindsay, D. B. Published by Butterworth Heinmann, Oxford. This states that low correlations between marbling fat and tenderness (typically around 0.2) suggest the involvement of other factors. Some of these have been identified for example the tendency of muscles in lean carcases to cold shorten if chilling rates are rapid. Even so, significant variation in tenderness still remains after the effect of all known factors are removed and a search for the cause of this is becoming more important.

In accordance with one aspect of the present invention, a method of obtaining information relating to the eating quality of a body comprising a hot or cold meat carcass, raw or cooked meat or live animal comprises injecting an acoustic signal into the body; monitoring the effect of the meat on at least one characteristic of the acoustic signal propagated into the meat; and applying the monitored effects to a predetermined algorithm relating eating quality as determined by human panel analysis to monitored acoustic effects to indicate the eating quality of the meat under test.

We have found very surprisingly that the toughness of the meat, and hence its future eating quality, is closely correlated with the effect of the meat on injected acoustic signals, particularly ultrasound. The characteristics can include time of flight, and/or scatter and/or attenuation of the ultrasound; and/or the reflection coefficient between the tissue and a known material. The preferred characteristics are attenuation and reciprocal of acoustic velocity which have the most significant correlations with taste panel assessment of eating quality.

Preferably, the result of this method will be combined with other investigative techniques of conventional types to produce an overall assessment of eating quality.

Typically, applying the predetermined algorithm comprises comparing the monitored effects with a previously determined table containing data defining a predetermined relationship between eating quality of meat carcasses and their effect on acoustic signals.

The methods are particularly suited to predict eating quality of cooked meat by inspecting uncooked carcasses.

Preferably, the acoustic signals are in the ultrasonic range, 40 KHz to 20 MHz, most preferably 1–10 MHz although frequencies outside this range are also suitable.

The acoustic signals injected into the body could be monitored by one or more transducers mounted on the surface of the carcass or animal and/or by one or more transducers within the carcass. In some cases where, for example, only scattering is to be monitored then the same transducer could be used for injecting and monitoring the acoustic signals. In other cases, however, a pair of transducers are provided.

In accordance with a second aspect of the invention an acoustic probe assembly comprises a pair of arms adapted for insertion into a meat carcass, the arms carrying respective means for coupling acoustic signals into and receiving signals from the carcass; and further means for coupling acoustic signals to the surface of a carcass and for monitoring scattering of the acoustic signals.

Preferably, the two arms are connected to each other by a cross-member so that the assembly has a generally U-shaped form, the cross-member forming a handle. This ensures that the two arms are rigidly held at a fixed and known separation (the separation is preferably adjustable) and the transmitted signal impinges on the receiver.

Preferably, the means carried by the arms will cause acoustic signals to be injected in the direction of a line connecting the two arms.

In one case, one arm may be adapted to inject acoustic energy into the carcass while the other is adapted to detect acoustic energy. Preferably, however, each arm carries means for both injecting and receiving acoustic energy.

In some cases, each arm may carry a transducer, for example respective piezo-electric elements, but it has been found more convenient to provide each arm with a sound guide for transmitting ultrasound from positions remote from the end of each arm at which ultrasonic transducers are provided.

Some examples of methods and apparatus according to the invention will now be described with reference to the accompanying drawings, in which.

Figure 1A:
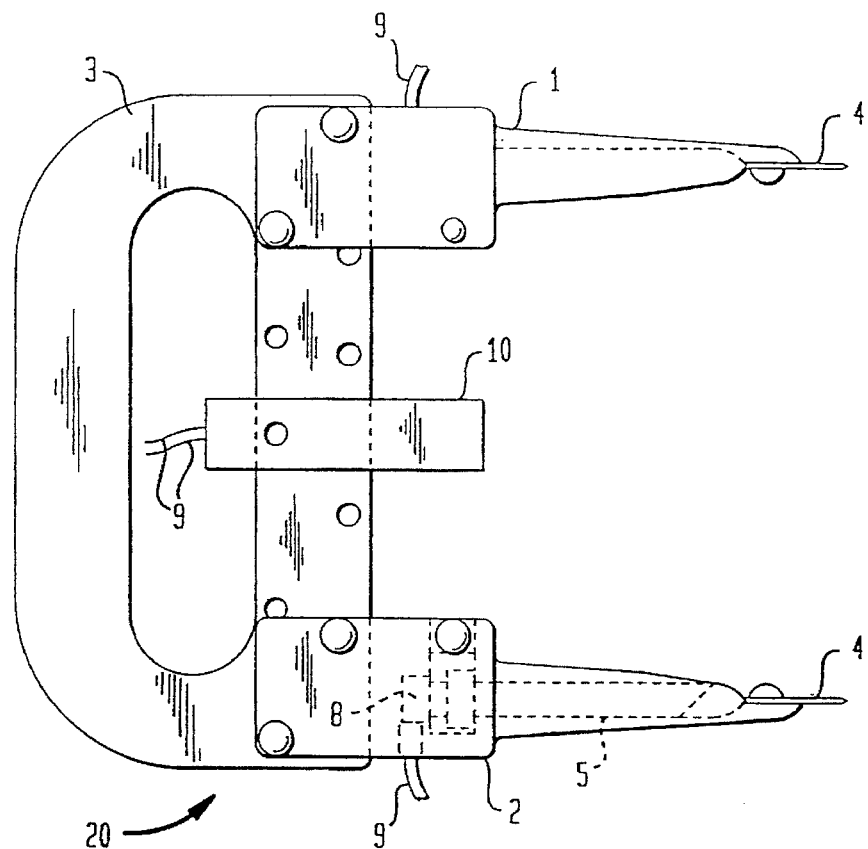
FIG. 1A illustrates a probe assembly.
Figure 1B:
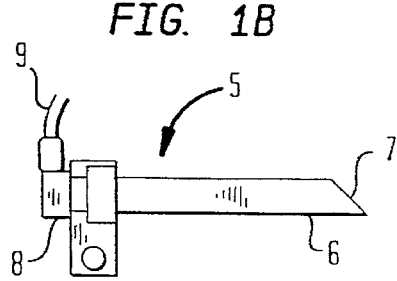
FIG. 1B illustrates a probe.
Figure 1C:
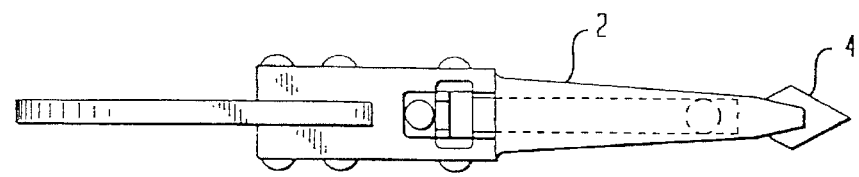
FIG. 1C illustrates one of the probe arms in more detail.
Figure 3:
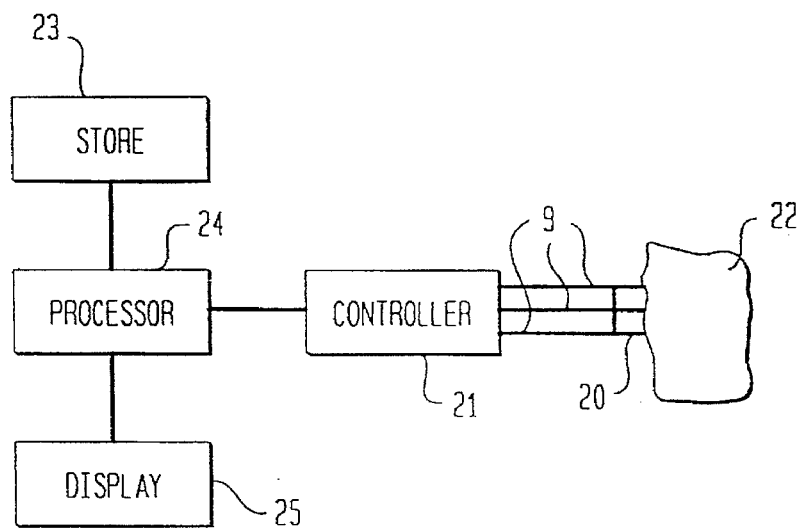
FIG. 3 is a block diagram of an example of the apparatus.

The probe assembly 20 shown in FIG. 1 has a pair of arms 1, 2 connected to a handle section 3. The lateral spacing between the arms 1, 2 can be varied by varying the positions at which the arms 1, 2 are mounted to the handle 3. Each arm 1, 2 carries at its leading end a penetration blade 4 (FIG. 1C). Each arm 1, 2 is hollow and within each arm is mounted an ultrasound generating and monitoring unit 5. Each unit 5 comprises a polystyrene waveguide 6 (FIG. 1B) having at its leading end an angled reflecting surface 7 from which ultrasound is injected into the tissue in use (or received), the reflecting surfaces being coated with a thin piezo-electric ceramic in order to produce a highly reflective surface. The other end of the sound guide 6 is coupled to a piezo-electric transducer 8 coupled via wires 9 to an ultrasound controller 21 (FIG. 3).

The assembly also includes an ultrasound generating and monitoring unit 10 which in use rests against the surface of the tissue for injecting and measuring back scattering and is connected to the controller 21 via wires 9.

In use, the probe assembly 20 shown in FIG. 1 is thrust into the tissue of a carcass 22 at a desired position (to be described below) following which the ultrasound measurements are taken.

FIG. 2 illustrates a number of alternative transducer configurations (to the FIG. 1 arrangement) which could be used with the invention. These arrangements might be used in conjunction with internal probes or they could be used as internal probes themselves with, if necessary, external transducers that could act simply as receivers or active transmitters/receivers.

Figure 2A:
FIGS. 2a–2d illustrate various transducer arrays.

The simplest example is shown in FIG. 2a and consists of a single transducer for transmitting and receiving acoustic energy. This could be placed on the surface of the meat or internally.

Figure 2B:

FIG. 2b illustrates a single array of transducers which might be mounted in practice on a suitable support and again which could be located and used on the surface of the meat or internally or even both.

Figure 2C:

FIG. 2c illustrates the use of an opposed pair of transducers facing one another and again these may be positioned in use on the surface of the meat or one or both internally of the meat.

Figure 2D:
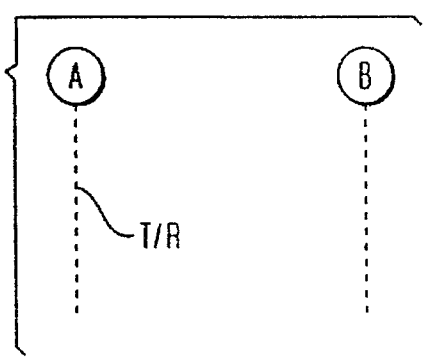

Finally, FIG. 2d illustrates the use of a pair of opposed arrays of transducers facing one another. In this case, the element (or bank of elements) labelled T/R might be used as the transmitter. Back-scattered signals could be monitored by the individual elements or banks of elements of array A giving not only magnitude and position information about the scatterers but also some information about the angular dependence of the back-scattering. T/R might be at any desired position on the array and its position could be varied.

A signal transmitted by T/R will be received by array B some time later. The delay, magnitude of the signal (in straight-through transmission and to the sides) will provide information about the speed of propagation, the signal attenuation and forward scattering of the tissue, including the angular dependence.

In another use of the arrangement, the direction of the transmitted beam might be swung through angles about the normal direction by appropriate phasing of the excitation of individual elements of the array "A". The back-scattered and forward-scattered signals might then be monitored as a function of angle. One would expect the back-scattering to be a maximum when the beam were aligned perpendicular to the fibre direction and this angle and the magnitude of the scattering and its angular dependence will give further information about the scatterers.

In a further use of this arrangement the position of bone interposed between the two arrays might be determined by the position of the shadows cast by the bone on a receiver array. Appropriate transducers might be used to direct the ultrasound through a region in which bone is absent. In a simpler version of this arrangement the array might be used like a "paint brush" transducer to produce of broad beam only partly obscured by the bone.

It is important to note the benefits of using only external transducers:

a) The measurements might be used on the living animal as well as the carcass or tissue.

b) There would be no problems with cross contamination of meat or the possibility of surface microbial contaminants being buried deep within the tissue.

Some examples of investigations into correlation between eating quality and effects on ultrasound will now be described.

Preliminary tests: Initial measurements were carried out at approximately 20° C. in caster oil and glycerol using water as a calibrant.

Measurement of carcasses: Ultrasonic measurements of beef were made with a two pronged probe only within 1 hour of slaughter and at 48 hours post slaughter. The probe was inserted just caudal to the last rib in the central region of the muscle with the direction of propagation first parallel and then perpendicular to the spine.

Ultrasonic measurements of pig carcasses were made at about 30 minutes post slaughter and at 24 hours. Measurements with the two pronged probe were made in the centre of the muscle just caudal to the last rib and with the direction of ultrasound propagation parallel to the spine. Measurements of ultrasound backscatter and fat thickness were made with a surface probe as described below.

Measurement of backscattering: A 3.5 MHz, single element 10 mm diameter, medium focus transducer (Diagnostic Sonar, Edinburgh) was used with a USD10 digital flaw detector (Wells Krautkramer, Letchworth) to provide A-mode signals of the back fat layers and Longissimus Thoracis et Lumborum.

a) Backfat thickness: The transducer was placed at the level of the last rib in the region of the P2 measurement and the gain of the USD10 adjusted to give an "on-screen" presentation of the fat layers and the signal recorded. A threshold was set at 0.8, 0.6, 0.4 and 0.2 and the time read off at intersection of the threshold with the final falling edge of the signal. P2 fatness is a measure of the thickness of fat and rind over the loin (or eye) muscle in mm. The measurement is taken at a position 6.5 cm away from the carcass mid-line at a location over the head of the last rib.

b) Intramuscular scattering: With the transducer at the P2 position, the gain of the USD10 was increased to display intramuscular scattering and the signal recorded. The signal was corrected for the gain setting oft he USD10 and a time corrected gain applied. Time windows were selected over which maximum, minimum, mean, standard deviation, coefficient of variation and root mean square amplitude were calculated. In the hot carcass the window ranged from 43.4 to 52.5 μs and the cold carcass from 37.4 to 52.5 μs. The factor used in the time corrected gain was exp (0.02t) where t is the time in μs from excitation of the transducer.

Correlations with Carcass Quality Traits

Beef

It was noticed that the acoustic properties of the polystyrene waveguides 6 were markedly temperature dependent and during the course of the beef experiment it was decided to make calibration measurements in water at 37° C. for the "hot" carcasses and at 0° C. for the "cold" carcasses. The probe was also maintained at these temperatures between measurements. Even so, there were significant correlations between ultrasonic measurements and quality traits in beef (Table 1). Notice particularly the correlations between ultrasound attenuation of the hot tissue and % intramuscular lipid and instrumental measurements of meat texture (Table 1). Attenuation in the cold tissues was correlated with various pH and colour measurements of the raw tissue and with instrumental measurements of texture (Table 1).

Most importantly, a correlation was seen between taste panel juiciness score (JUC6) and the reciprocal of the velocity of sound in the cold carcass (CVRVS) and between taste panel texture score (TXT6) and the reciprocal of the velocity of sound in the hot carcass (HVRVS).

Overall, a best multiple correlation (r) of 0.52 was seen between hot carcass measurements and taste panel tenderness score.

Pork

Tables 2 and 3 show the significant ($P<0.05$) correlations between ultrasonic measurements of the hot and cold carcasses and carcass quality traits.

Fat thickness: The highest correlations were obtained between the ultrasonic estimates of fat thickness and P2 measured by Intrascope. There was some indiction overall that the extreme threshold levels were less reliable than the mid-range thresholds and a threshold at 40% of the maximum yielded a consistently high correlation in both hot and cold carcasses and in both groups.

% intramuscular lipid: Significant correlations with intramuscular lipid were obtained with the reciprocal speed in the hot carcass, attenuation in the hot muscle, ultrasonic measurements of fat thickness, and one measure of intramuscular scattering.

A comparison of simple and multiple regression predictions of intramuscular lipid is given in Table 5.

% drip: The negative correlation ($r=-0.48$, Group A: $r=-0.35$, Group B) between the reflection coefficient for the polystyrene/tissue interface in the warm carcass was probably caused by a tendency for better acoustic coupling (less air) to be accomplished by the wetter (i.e. more drip-producing) tissue. Those tissues tended to give the lowest reflection coefficient, hence the negative correlation.

Taste panel assessments: Negative correlations between attenuation and taste panel texture scores were observed for "hot" and "cold" tissue measurements in both groups of carcasses (Tables 2 and 3). Negative correlations were also apparent in hot and cold tissues between attenuation and overall acceptability score, and in the cold tissue between attenuation and flavour (Tables 2 and 3).

Although the magnitude of these correlations were low, so were the correlations between the standard instrumental tests of the cooked meat and taste panel texture scores (Table 4). Multiple regression improved the precision of the ultrasonic correlations further (Table 5), the best multiple correlation on the basis of the ultrasonic measurements of the cold carcass ($r=0.55$, Group A) is comparable with the precision of the conventional instrumental measures of texture of the cooked meat (0.53 to 0.58, Table 4). Analysis of Group B allowed inclusion of the ultrasonic measurements of scattering in multiple regression and the multiple correlation coefficient with that group was higher (e.g. in the cold carcass: $r=0.68$, which compares with the conventional measures which range from 0.52 to 0.63, Table 4).

Now that it has been shown that there is a significant correlation between certain effects of hot and cold carcasses on ultrasound with eating quality, a store 23 (FIG. 3) can be set up defining a concordance between the results of various empirical ultrasonic tests and the corresponding empirically determined eating quality factors.

In operation, a processor 24 causes a controller 21 to inject suitable ultrasound signals into the carcass 22 and then monitors the detected signals which are passed to it via the controller. The processor 24 then obtains from the store 23 the eating quality values corresponding to the monitored ultrasonic values and either displays these in a raw form on a display 25 or carries out further processing using other data obtained from the carcass to generate a resultant "eating quality" factor.

In a preferred arrangement, the store 23 could be used to maintain a library of ultrasonic data on carcasses of known eating quality and the processor could use advanced statistical techniques, for example neural networks, to determine the best match carcass and hence predict quality.

The temperature dependence noted above can be corrected for if temperature is measured simultaneously with measurement of ultrasonic parameters.

In the Tables below, a value of "0" indicates no correlation while a value of "1" indicates perfect correlation. "N" indicates the number of samples or animals used.

| Key to Table 1 | |
| --- | --- |
| Column headings: | |
| VARI | variation |
| FAT % | % lipid in LTL |
| DRP % | % drip from LTL |
| YLD6 | Volodkevitch yield |
| CMP6 | Volodkevitch compression |
| AR6 | Volodkevitch work done |
| TXT6 | Taste panel texture score |
| JUC6 | Taste panel juiciness score |
| Row headings: | |
| Initial letter H refers to "hot" carcass measurement | |
| Initial letter C refers, to "cold" carcass measurement | |
| Second letter H refers to measurement perpendicular to spine | |
| Second letter V refers to measurement parallel to spine | |
| Subsequent letters: | |
| RVS | reciprocal of the velocity of ultrasound |
| RRXY | mean amplitude reflection coefficient |
| OADB | "amplitude" attenuation coefficient |
| ORDB | "rms" attenuation coefficient |
| PDB27 | attenuation coefficient at 2.7 MHz |
| PDB30 | attenuation coefficient at 3.0 MHz |
| PDB32 | attenuation coefficient at 3.2 MHz |
| PDB34 | attenuation coefficient at 3.4 MHz |

-continued

| Key to Table 1 | |
|---|---|
| PDB36 | attenuation coefficient at 3.6 MHz |

TABLE 1

Simple correlations for beef (see key to Table 1)
N = 48

| VARI | FAT % | DRP % | YLD6 | CMP6 | AR6 | TXT6 | JUC6 |
|---|---|---|---|---|---|---|---|
| HHOADB | 0.33 | * | * | * | * | * | * |
| HHORDB | 0.39 | * | * | * | −0.34 | * | * |
| HHPDB27 | 0.46 | * | * | * | −0.38 | * | * |
| HHPDB30 | 0.44 | * | * | * | −0.38 | * | * |
| HHPDB32 | 0.41 | * | * | * | −0.38 | * | * |
| HHPDB34 | 0.36 | * | * | * | −0.35 | * | * |
| HHPDB36 | 0.30 | * | * | * | −0.30 | * | * |
| HVRVS | * | * | * | * | * | −0.31 | * |
| HVOADB | * | −0.34 | * | * | * | * | * |
| CHRVS | * | * | * | * | 0.35 | * | * |
| CHOADB | * | * | −0.36 | −0.35 | −0.40 | * | * |
| CHORDB | * | * | −0.37 | −0.35 | −0.40 | * | * |
| CVRVS | * | * | 0.39 | 0.37 | 0.39 | * | 0.35 |
| CVRRXY | * | * | 0.30 | * | * | * | * |
| CVOADB | * | −0.37 | * | * | * | * | * |
| CVORDB | * | −0.35 | * | * | * | * | * |

*indicates non-significant correlation (p > 0.05).
r ≧ 0.28 correlation significant at p < 0.05 level
r ≧ 0.37 correlation significant at p < 0.01 level
r ≧ 0.46 correlation significant at p < 0.001 level

Key to Tables 2 and 3

Column headings:

| | |
|---|---|
| VARI | variable |
| FAT % | % intramuscular fat in LTL |
| HUE | hue (colour) |
| DRP % | drip loss % |
| YLD4 | Volodkevitch yield |
| CMP4 | Volodkevitch compression |
| AR4 | Volodkevitch work done |
| TEX4 | Warner-Bratzler measurement |
| ODOR | pork odour intensity in fat |
| OINT | abnormal odour intensity in fat |
| COL | colour of lean |
| TEX | texture of lean |
| FLAV | pork flavour intensity of lean |
| OVER | overall liking |

Row headings:

If the first letter is H, measurement made on the hot carcass
If the first letter is C, measurement made on the cold carcass
Subsequent letters:

| | |
|---|---|
| RVS | reciprocal of the speed of ultrasound |
| RRXY | mean reflection coefficient |
| OADB | "peak amplitude" attenuation |
| ORDB | "rms" attenuation |
| PDB27 | attenuation at 2.7 MHz |
| PDB30 | attenuation at 3.0 MHz |
| PDB32 | attenuation at 3.2 MHz |
| PDB34 | attenuation at 3.4 MHz |
| PDB36 | attenuation at 3.6 MHz |
| PDB38 | attenuation at 3.8 MHz |
| PDB41 | attenuation at 4.1 MHz |
| PDB43 | attenuation at 4.3 MHz |
| P20 | ultrasonic measurement of fat thickness using 0.2 threshold |
| P40 | ultrasonic measurement of fat thickness using 0.4 threshold |
| P60 | ultrasonic measurement of fat thickness using 0.6 threshold |
| P80 | ultrasonic measurement of fat thickness using 0.8 threshold |
| MMIN | minimum amplitude of backscattered signal |
| MMAX | maximum amplitude of backscattered signal |
| MRAN | range (max–min) of backscattered signal |
| MMEAN | mean amplitude of backscattered signal |
| MSD | standard deviation of the backscattered signal |
| RMSMUS | rms amplitude of backscattered signal |
| CV % | coefficient of variation of backscattered signal |

TABLE 2

Simple correlations for pigs (see key to Tables 2 and 3)
Group A, N = 59

| VARI | FAT % | DRP % | YLD4 | CMP4 | AR4 | TEX4 | OINT | COL | TEX | FLAV | OVER |
|---|---|---|---|---|---|---|---|---|---|---|---|
| HRVS   | 0.28 | −0.31 | 0.32 | 0.31 | 0.39 | 0.27 | *    | *    | *     | *     | *     |
| HRRXY  | *    | −0.48 | *    | *    | *    | *    | *    | *    | *     | *     | *     |
| HOADB  | *    | *     | *    | *    | *    | *    | *    | 0.27 | −0.30 | *     | *     |
| HORDB  | *    | *     | *    | *    | *    | *    | *    | *    | −0.29 | *     | *     |
| HPDB27 | *    | *     | *    | *    | *    | *    | *    | 0.27 | −0.28 | *     | *     |
| HPDB30 | *    | *     | *    | *    | *    | *    | *    | 0.27 | −0.29 | *     | *     |
| HPDB32 | *    | *     | *    | *    | *    | *    | *    | 0.27 | −0.30 | *     | *     |
| HPDB34 | *    | *     | *    | *    | *    | *    | *    | *    | −0.29 | *     | *     |
| HPDB36 | 0.35 | *     | *    | *    | *    | *    | *    | *    | −0.28 | *     | *     |
| HPDB38 | 0.43 | −0.26 | *    | *    | *    | *    | *    | *    | *     | *     | *     |
| HPDB41 | 0.47 | −0.29 | *    | *    | *    | *    | *    | *    | *     | *     | *     |
| HPDB43 | 0.46 | −0.29 | *    | *    | *    | *    | *    | *    | *     | *     | *     |
| HP40   | 0.41 | *     | *    | *    | *    | *    | 0.27 | *    | *     | *     | *     |
| HP60   | 0.39 | *     | *    | *    | *    | *    | *    | *    | *     | *     | *     |
| HP80   | 0.31 | *     | *    | *    | *    | *    | *    | *    | *     | *     | *     |
| COADB  | *    | *     | *    | *    | *    | 0.27 | *    | 0.31 | −0.31 | −0.38 | −0.26 |
| CORDB  | *    | *     | *    | *    | *    | 0.32 | *    | 0.30 | −0.35 | −0.39 | −0.27 |
| CPDB27 | *    | *     | *    | *    | *    | 0.39 | *    | 0.32 | −0.40 | −0.35 | −0.27 |
| CPDB30 | *    | *     | *    | *    | *    | 0.37 | *    | 0.31 | −0.37 | −0.35 | −0.27 |
| CPDB32 | *    | *     | *    | *    | *    | 0.34 | *    | 0.31 | −0.33 | −0.36 | −0.26 |
| CPDB34 | *    | *     | *    | *    | *    | 0.29 | *    | 0.29 | −0.27 | −0.35 | *     |
| CPDB36 | *    | *     | *    | *    | *    | *    | *    | *    | *     | −0.34 | *     |
| CPDB38 | *    | *     | *    | *    | *    | *    | *    | *    | *     | −0.30 | *     |
| CP20   | 0.49 | *     | *    | *    | *    | *    | *    | *    | *     | *     | *     |
| CP40   | 0.39 | *     | *    | *    | *    | *    | *    | *    | *     | *     | *     |
| CP60   | 0.47 | *     | *    | *    | *    | *    | *    | *    | *     | *     | *     |
| CP80   | 0.31 | *     | *    | *    | *    | *    | *    | *    | *     | *     | *     |

*indicates non-significant correlation (p > 0.05)
r ≧ 0.26 correlation significant at p < 0.05 level
r ≧ 0.33 correlation significant at p < 0.01 level
r ≧ 0.41 correlation significant at p < 0.001 level

TABLE 3

Simple correlations for pigs (see key to Tables 2 and 3)
Group B, N = 39

| VARI | FAT % | HUE | DRP % | YLD4 | CMP4 | AR4 | TEX4 | ODOR | OINT | COL | TEX | FLAV | OVER |
|---|---|---|---|---|---|---|---|---|---|---|---|---|---|
| HRVS    | *    | * | −0.35 | *    | *    | 0.40 | *    | *    | *    | *    | *     | *     | *     |
| HRRXY   | *    | * | −0.35 | *    | *    | *    | *    | *    | 0.37 | *    | *     | *     | *     |
| HOADB   | *    | * | *     | *    | *    | *    | *    | *    | *    | 0.31 | −0.44 | *     | −0.42 |
| HORDB   | *    | * | *     | *    | *    | *    | *    | *    | *    | *    | −0.42 | *     | −0.40 |
| HPDB27  | *    | * | *     | *    | *    | *    | *    | *    | *    | *    | −0.39 | *     | −0.36 |
| HPDB30  | *    | * | *     | *    | *    | *    | *    | *    | *    | 0.31 | −0.41 | *     | −0.38 |
| HPDB32  | *    | * | *     | *    | *    | *    | *    | *    | *    | 0.31 | −0.42 | *     | −0.38 |
| HPDB34  | *    | * | *     | *    | *    | *    | *    | *    | *    | *    | −0.42 | *     | −0.37 |
| HPDB36  | 0.43 | * | *     | *    | *    | *    | *    | *    | *    | *    | −0.41 | *     | −0.32 |
| HPDB38  | 0.54 | * | *     | *    | *    | *    | *    | *    | *    | *    | −0.37 | *     | *     |
| HPDB41  | 0.59 | * | −0.33 | *    | *    | *    | *    | *    | *    | *    | −0.32 | *     | *     |
| HPDB43  | 0.57 | * | −0.33 | 0.33 | 0.34 | *    | *    | *    | *    | *    | *     | *     | *     |
| HP40    | 0.43 | * | *     | *    | *    | *    | *    | *    | *    | *    | *     | *     | *     |
| HP60    | 0.45 | * | *     | *    | *    | *    | *    | *    | *    | *    | *     | *     | *     |
| HMMIN   | 0.44 | * | *     | *    | *    | *    | 0.38 | *    | *    | *    | −0.40 | *     | *     |
| HMMAX   | *    | * | *     | *    | *    | *    | 0.37 | *    | *    | *    | −0.33 | *     | *     |
| HMRAN   | *    | * | *     | *    | *    | *    | 0.35 | *    | *    | *    | *     | *     | *     |
| HMMEAN  | *    | * | *     | *    | *    | *    | 0.39 | *    | *    | *    | −0.33 | *     | *     |
| HMSD    | *    | * | *     | *    | *    | *    | 0.32 | *    | *    | *    | *     | *     | *     |
| HRMSMUS | *    | * | *     | *    | *    | *    | 0.37 | *    | *    | *    | −0.32 | *     | *     |
| CRRXY   | *    | * | −0.33 | *    | *    | *    | *    | *    | *    | *    | *     | *     | *     |
| COADB   | *    | * | −0.34 | *    | *    | *    | *    | *    | *    | 0.39 | −0.35 | −0.39 | −0.34 |
| CORDB   | *    | * | *     | *    | *    | *    | *    | *    | *    | 0.38 | −0.39 | −0.38 | −0.34 |
| CPDB27  | *    | * | *     | *    | *    | *    | 0.38 | *    | *    | 0.37 | −0.46 | −0.34 | −0.34 |
| CPDB30  | *    | * | *     | *    | *    | *    | 0.35 | *    | *    | 0.37 | −0.42 | −0.34 | −0.34 |
| CPDB32  | *    | * | *     | *    | *    | *    | 0.32 | *    | *    | 0.37 | −0.37 | −0.33 | −0.33 |
| CPDB34  | *    | * | *     | *    | *    | *    | *    | *    | *    | 0.37 | *     | −0.32 | −0.32 |

TABLE 3-continued

Simple correlations for pigs (see key to Tables 2 and 3)
Group B, N = 39

| VARI | FAT % | HUE | DRP % | YLD4 | CMP4 | AR4 | TEX4 | ODOR | OINT | COL | TEX | FLAV | OVER |
|---|---|---|---|---|---|---|---|---|---|---|---|---|
| CPDB36 | * | * | * | * | * | * | * | * | * | 0.36 | * | * | * |
| CPDB38 | * | * | * | * | * | * | * | * | * | 0.35 | * | * | * |
| CPDB41 | * | −0.33 | * | * | * | * | * | * | * | * | * | * | * |
| CPDB43 | * | −0.32 | * | * | * | * | * | −0.32 | * | * | * | * | * |
| CP20 | 0.50 | * | −0.36 | * | * | * | * | * | * | * | * | * | * |
| CP40 | 0.36 | * | * | * | * | * | * | * | * | * | * | * | * |
| CP60 | 0.45 | * | * | * | * | * | * | * | * | * | * | * | * |
| CMMIN | * | * | * | * | * | * | * | * | * | * | 0.37 | * | * |
| CCV % | * | * | * | * | * | * | * | * | * | * | −0.32 | * | * |

*indicates non-significant correlation (p > 0.05)
r ≧ 0.31 correlation significant at p < 0.05 level
r ≧ 0.41 correlation significant at p < 0.01 level
r ≧ 0.50 correlation significant at p < 0.001 level

TABLE 4

Comparison of the precision of predicting taste panel texture score for pork for either ultrasonic measurement of the 'hot' or 'cold' carcass or Volodkevitch and Warner Bratzler measurement of the cooked meat. All data are simple correlation coefficients.

| | | n = 39 | | n = 59 | |
|---|---|---|---|---|---|
| | | hot carcass | cold carcass | hot carcass | cold carcass |
| Ultrasonic | attenuation | −0.40 | −0.47 | −0.30 | −0.40 |
| | scattering | −0.42 | −0.37 | — | — |
| | | cooked tissue | | cooked tissue | |
| Volodkevitch | Yield | −0.52 | | −0.53 | |
| | Compression | −0.55 | | −0.55 | |
| | Work done | −0.63 | | −0.58 | |
| | Warner Bratzler | −0.57 | | −0.57 | |

TABLE 5

The modulus of simple and multiple correlation coefficients for predicting taste panel texture scores and % fat in LTL from ultrasonic measurements of the carcass.

| | Taste panel texture scores | | | | % lipid | | | |
|---|---|---|---|---|---|---|---|---|
| | n = 39 | | n = 59 | | n = 39 | | n = 59 | |
| | Hot | Cold | Hot | Cold | Hot | Cold | Hot | Cold |
| 'best' simple regression | 0.40 | 0.47 | 0.30 | 0.40 | 0.59 | 0.50 | 0.47 | 0.47 |
| 'best' multiple regression | 0.74 | 0.68 | 0.38 | 0.55 | 0.88 | 0.76 | 0.59 | 0.66 |

What is claimed is:

1. A method for obtaining information relating to the eating quality of meat, comprising the steps of:
   injecting an acoustic signal into the meat;
   monitoring the effect of the meat on at least one characteristic of said acoustic signal propagated into the meat; and
   applying said monitored effects to a predetermined algorithm relating eating quality as determined by human panel analysis to monitored acoustic effects to indicate the eating quality of the meat under test.

2. A method according to claim 1, wherein said acoustic signal comprises ultrasound.

3. A method according to claim 1, wherein said at least one characteristic comprises one or more of the time of flight, scatter, and attenuation of the injected signal.

4. A method according to claim 1, wherein said applying step comprises comparing said monitored effects with a previously determined table containing data defining a predetermined relationship between the eating quality of meat and said monitored acoustic effects.

5. A method according to claim 1, wherein the meat comprises an uncooked carcass and said predetermined algorithm defines the eating quality of cooked meat from the carcass.

6. A method according to claim 1, wherein said acoustic signal is in the range 40 KHz to 20 MHz.

7. A method according to claim 6, wherein said acoustic signal is in the range of 1 to 10 MHz.

8. A method according to claim 1, wherein said predetermined algorithm defines eating quality at least partly by texture scores.

9. A method according to claim 1, wherein said predetermined algorithm defines eating quality at least partly by juiciness scores.

10. A method according to claim 4, wherein said predetermined algorithm defines eating quality at least partly by tenderness scores.

11. An acoustic probe assembly, comprising:
    a pair of arms configured to be inserted into a meat carcass;
    means, disposed in each arm, for coupling a plurality of first acoustic signals into and for receiving said plurality of first acoustic signals from said meat carcass; and
    means, disposed in each arm, for coupling a plurality of second acoustic signals to the surface of said meat carcass and for monitoring scattering of said plurality of second acoustic signals.

12. An assembly according to claim 11, wherein said pair of arms are connected to each other by a cross-member so that the assembly is U-shaped, said cross-member forming a handle.

13. An assembly according to claim 11, wherein said means for coupling a plurality of first and second acoustic signals are configured so that said first and second acoustic signals are injected in said meat carcass in the direction of a line connecting said pair of arms.

14. An assembly according to claim 11, wherein said plurality of first and second acoustic signals comprise ultrasonic signals.

15. An apparatus for obtaining information relating to the eating quality of meal, comprising:

means for injecting an acoustic signal into the meat;

means for monitoring the effect of the meat on at least one characteristic of said acoustic signal propagated into the meat; and means for applying the monitored effects to a predetermined algorithm relating eating quality as determined by human panel analysis to monitored acoustic effects to indicate the eating quality of the meat under test.

16. An apparatus according to claim 15, wherein said applying means comprises:

a processor; and a store, said store containing information defining the relationship between said monitored acoustic effects and eating quality values.

17. An apparatus according to claim 16, wherein said eating quality values comprise texture scores.

18. An apparatus according to claim 16, wherein said eating quality values comprise juiciness scores.

19. An apparatus according to claim 16, wherein said eating quality values comprise tenderness scores.

* * * * *